(12) United States Patent
Marino et al.

(10) Patent No.: US 6,743,586 B2
(45) Date of Patent: Jun. 1, 2004

(54) RAPID FLUORESCENCE DETECTION OF BINDING TO NUCLEIC ACID DRUG TARGETS LABELLED WITH HIGHLY FLUORESCENT NUCLEOTIDE BASE ANALOGS

(75) Inventors: John P. Marino, Silver Spring, MD (US); James T. Stivers, Baltimore, MD (US); Karen Lacourciere, Silver Spring, MD (US)

(73) Assignee: The United States of America as represented by the Secretary of the Commerce, Washington, DC (US)

( * ) Notice: Subject to any disclaimer, the term of this patent is extended or adjusted under 35 U.S.C. 154(b) by 43 days.

(21) Appl. No.: 09/983,742

(22) Filed: Oct. 25, 2001

(65) Prior Publication Data

US 2003/0165846 A1 Sep. 4, 2003

Related U.S. Application Data

(60) Provisional application No. 60/270,550, filed on Feb. 22, 2001, and provisional application No. 60/264,836, filed on Jan. 29, 2001.

(51) Int. Cl.$^7$ .................... C12Q 1/68; G01N 33/53; G01N 33/566; C07K 14/00; C07H 21/02; C07H 21/04

(52) U.S. Cl. .................... 435/6; 435/7.1; 436/501; 530/300; 530/350; 530/387.1; 536/23.1; 536/24.3

(58) Field of Search ............... 435/6, 7.1, 810, 435/968; 436/501; 530/300, 350; 536/23.1, 24.3

(56) References Cited

U.S. PATENT DOCUMENTS

| | | | |
|---|---|---|---|
| 5,712,096 A | | 1/1998 | Stern et al. |
| 5,766,550 A | * | 6/1998 | Kaplan et al. |
| 6,057,095 A | | 5/2000 | Arrigo |
| 6,096,502 A | | 8/2000 | Lee |
| 6,153,382 A | | 11/2000 | Karn et al. |
| 6,172,214 B1 | | 1/2001 | Brenner |
| 6,395,541 B1 | * | 5/2002 | Hall et al. |

OTHER PUBLICATIONS

Kevin D. Raney, A fluorescence–based assay for monitoring helicase actiity Jul. 1994,.*

* cited by examiner

Primary Examiner—Stephanie W. Zitomer

(57) ABSTRACT

The present invention is a method of identifying ligands that interact will cellular processes involved in the life-cycle of HIV. In particular, an oligonucleotide, corresponding to specific RNA sequence within an infected cell, is modified by the substitution of 2-aminopurine. As a result, interactions between the oligonucleotide and the ligand can be measured via fluorescence. This technique can be use to find inhibitors of binding between rev and its response element (RRE), dimerization initiation sequences, and topoisomerases and DNA.

22 Claims, 2 Drawing Sheets

RAPID FLUORESCENCE DETECTION OF BINDING TO NUCLEIC ACID DRUG TARGETS LABELLED WITH HIGHLY FLUORESCENT NUCLEOTIDE BASE ANALOGS

CROSS REFERENCE TO RELATED APPLICATIONS

This is a non-provisional application incorporating references U.S. Ser. No. 60/270,550, filed Feb. 22, 2001, and U.S. Ser. No. 60/264,836, filed Jan. 29, 2001, both of which are incorporated by reference in their entirety, the benefit of the filing dates of the provisional applications being defined under 35 USC § 119.

FIELD OF THE INVENTION

This invention pertains to a method for selective substitution of highly fluorescent nucleotide base analogs within a sequence of nucleic acid drug targets. The substitution is particularly selected such that the base can be used as a probe to monitor and screen for interactions of ligands with a nucleic acid target.

BACKGROUND

The development of specific inhibitors of protein-RNA interactions, that are unique and required for retroviral viability, is of significant interest to pharmaceutical industries since these complexes provide new and potentially powerful targets to inhibit retroviral infection.

As described in U.S. Pat. No. 6,153,382, herein incorporated by reference, the HIV genome is tightly compressed. At least 30 different RNA transcripts are produced by splicing using the six splice acceptors and two splice donor sequences. The structural proteins encoded by HIV are chemically similar to those of the C-type retroviruses and, like them, are encoded as polyproteins by the gag (group antigen), pol (polymerase) and env (envelope) genes. Cleavage of the polyproteins by the viral protease or cellular enzymes generates eight functional virion proteins. In addition to these structural genes, HIV-1 also carries genes for three regulatory proteins, rev (regulator factor); and two proteins involved in virus maturation, vif (virion infectivity factor) and vpu (viral protein U). The vpr (viral protein R) gene encodes a low copy number virion component. In the closely related viruses HIV-2 and simian immunodeficiency virus (SIV), vpr is replaced by vpx (viral protein X), a unique virion protein.

Transcription of the HIV genome during virus replication shows distinct kinetic phases. The initial products of HIV gene expression are short, multiply spliced mRNAs approximately 1.8 to 2.0 kb in length, which encode the trans-acting regulatory proteins including rev. As infection by the virus develops, and the levels of the rev protein rise in the infected cells, mRNA production shifts progressively towards synthesis of a family of singly-spliced 4.3 kb mRNAs encoding env and other HIV gene products such as vif and vpr. Finally, late in the infection process, production switches to full-length, unspliced, transcripts that act both as the virion genomic RNA and the mRNA for the gag-pol polyprotein.

To achieve this control of gene expression, HIV relies on the interaction of cellular and virus-encoded trans-acting factors with cis-acting viral regulatory sequences. Initiation of transcription relies largely on the presence of binding sites for cellular transcription factors in the viral long terminal repeat (LTR). In contrast, the virally encoded regulatory proteins tat and rev exert their activity via cis-acting sequences encoded within HIV messenger RNAs. After a systematic search, a cis-acting sequence required for rev activity, was mapped to a complicated RNA stem-loop structure located within the env reading frame. This sequence has been named the rev-responsive element (RRE) and has been localized to a 234-nucleotide long sequence within the env gene. Similar regulatory proteins and target sequences are used by HIV-2 and SIV. The human T-cell leukemia (HTLV-1) virus rex gene product appears to function analogously to rev, and can functionally substitute for rev to promote viral gene expression.

The distinct kinetic phases of HIV transcription are now believed to reflect the intracellular levels of the regulatory proteins tat and rev. Initially, binding of host transcription factors to the LTR induced basal level transcription of the early mRNAs including tat. As tat levels rise, increased transcription from the LTR is stimulated by the trans-activation mechanism. This leads to further increases in tat levels, and also stimulates production of rev. Production of the viral structural proteins begins once rev levels have risen to sufficiently high levels to promote export of messenger RNAs carrying the RRE sequence. The HIV growth cycle may also include a latent stage where viral gene expression is silent because transcription from the viral LTR produces insufficient amounts of regulatory proteins to initiate the lytic growth cycle.

Rev recognition of the RRE RNA element, like tat recognition of HIV-1 trans activation region (TAR) RNA, is due to direct binding. Binding is tight ($K_D$=1-3 nM) and highly specific for the RRE. However, the binding behavior of rev to RRE is much more complex than the binding of tat to TAR RNA. As the concentration of rev increases, progressively larger complexes with RRE RNA are formed, whereas tat only forms one-to-one complexes with TAR RNA.

The simplest explanation for the RNA binding behavior of rev is that the protein binds initially to a high affinity site and that subsequently additional rev molecules occupy lower affinity sites.

Many methods for nucleic acid-protein binding assays, to measure interactions of, for example, RRE with rev, have been developed, such as gel electrophoresis, filter binding and chromatography. However, these procedures lack sufficient speed, sensitivity and accuracy to be useful as high-throughput binding assays. Additionally, fluorescence methods, such as fluorescence resonance energy transfer (FRET), provide many advantages, however do not detect both direct and indirect interactions of rev peptide or ligand binding that cause subtle conformational changes in the nucleic acid structure of RRE.

SUMMARY OF THE INVENTION

The present invention pertains to a generally useful approach for detecting and quantifying the interaction of nucleic acids with macromolecules and/or small molecule ligands that can be adapted into high-throughput screens (HTS). A fluorescence-based binding assay, i.e. fluorescence emission perturbation (FREP) has been developed that provides such a method for screening and optimizing inhibitors of nucleic-acid protein interactions that are potential and so far unexploited targets for anti-viral and anti-cancer drugs. The FREP method described and claimed herein, provides a general, rapid and sensitive fluorescence assay that allows the direct detection and quantification of the interaction of ligand with nucleic acid targets. Using the FREP assay, multiple binding classes of small molecules to nucleic acid targets can be directly detected, as well as specific inhibition of macromolecular interactions with nucleic acid targets by small molecule antagonists. The ability to detect both macromolecular (mostly protein) and small molecule binding using the same fluorescently labeled nucleic acid constructs allows the application of dual screening; where analysis for both direct binding of small molecules, as well as the potential competitive inhibition of the nucleic acid-protein interaction by these molecules may be assayed simultaneously.

In particular, the FREP binding assay, in one form, includes an RRE oligonucleotide labeled with the fluorescence adenosine analog, 2-aminopurine (2-AP) in specific nucleotide. Modified RRE oligonucleotides show measurable changes in fluorescence emission that can be directly correlated with rev and small molecule binding to RRE; thereby providing a general method for monitoring these binding interactions. Rev monomers (or small peptides derived from rev) act by first binding to a high affinity site within the response element (RRE), a 34-nucleotide stem-loop structure (stem-loop IIB) found in nuclear HIV-1 mRNA transcripts (FIG. 1).

The FREP method is applicable in the context of many nucleic acid systems. Specifically, however, the FREP method is particularly advantageous for use in measuring interactions with (1) the above-described HIV-1 RRE-rev system; (2) HIV-1 dimerization initiation sequences (DIS); and (3) topoisomerase DNA systems.

Previous studies have shown the 2-AP can be used as a valuable probe of the structure and dynamics of specific sites in DNA, as a monitor for enzyme-DNA interaction, and to study $Mg^{2+}$ dependent conformational changes in certain ribozymes. The fluorescence of 2-AP is usually highly quenched when it is stacked with other bases, but increases as much as 100 fold when fully exposed to solvent. Thus, the quantum yield of 2-AP is highly sensitive to changes in its microenvironment, which allows the detection of subtle conformational changes in the nucleic acid upon interaction with ligands. In addition, 2-AP is a generally non-perturbing substitution because it is similar in structure to adenine (6-aminopurine) and will form a thermodynamically equivalent base pair with uridine.

The FREP method of the invention has proven to be a more general and more easily applied approach for detecting and quantifying interactions with nucleic acids because the fluorescence base reporter groups do not need to directly interact with either the macromolecule or the small molecules to show a measurable change in fluorescence. Instead, subtle conformational changes in the nucleic acid structure caused by ligand binding could either directly or indirectly result in significant changes in the fluorescence intensity of the fluorescent base reported that could be used as a monitor for binding. This feature makes the FREP assay a more general reporting technique for binding interactions, than, for example, a specific FRET pair, allowing both for screening of direct small molecule RNA interactions, as well as for binding events that result in an inhibition of macromolecular complex formation. Moreover, the use of fluorescent nucleotide base labeling of the nucleic acid target allows screening of molecular libraries without any need for further labeling of macromolecules (proteins or peptides) or small molecules. This is a large advantage in terms of versatility and generality of this screening method. A summary comparison of the 2-AP FREP method of the invention with other conventional methods is shown in Table 1.

TABLE 1

| | Sensitivity | Versatility | Throughput | Cost |
|---|---|---|---|---|
| 2-AP Labeling | High | Very High | High | Low |
| Filter Binding Assay | High | Very Low | Low | High |
| Electrophoretic Mobility Shift Assay (EMSA) | High | Very Low | Very Low | High |
| Surface Plasmon Resonance | High | Low | Low | High |
| Fluorescence Resonance Energy Transfer (FRET) | Very High | Medium | High | Medium |

DETAILED DESCRIPTION

In a first embodiment, the RRE-rev model system is derived from a critical RNA-protein interaction in the viral life cycle. A 34mer stem-loop IIB of the rev Response Element (RRE), shown modified in FIG. 1 SEQ ID NO: 1, is conventionally known as a high affinity rev binding site. Nucleotides identified by previous studies as important for rev binding are circled. Nucleotide positions substituted with 2-aminopurine-2-O-methoyl roboside (2-AP) are boxed. A 17 amino acid arginine-rich region rev, amino acids 34 to 51, is known to specifically bind to RRE. This interaction is described in U.S. Pat. No. 6,153,382 to Karn et al., herein incorporated by reference in its entirety. Nucleotides A68 or U72 which are located in the high affinity rev binding site of stem-loop IIB of RRE, but which are not critical for peptide-RRE interaction, have been substituted with the highly fluorescent adenosine analog, 2-aminopurine (2-AP) shown below:

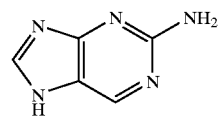

Experiments have shown that 2-AP substituted at these positions showed the largest fluorescence emission perturbation (FREP) upon binding of peptide (72AP-RRE SEQ ID NO: 4 reports on peptide binding) and small molecules (both 72AP-RRE and 68AP-RRE SEQ ID NO: 3report on small molecule binding) and therefore provides the most useful probes to detect these binding events. The fluorescence signal of the 2-AP reporter in the 72AP-RRE construct increases twofold upon binding of the rev peptide and is most sensitive position for detection of rev peptide binding. Although positions 68 and 72 are preferred, it is within the scope of the present invention to substitute any position in RRE, either in stem-loop IIB or elsewhere in the response element which results in a change fluorescence upon interacting with rev or other peptides.

The results obtained from interacting rev and other ligands with 68AP-RRE and 72AP-RRE show that substitution at these particular positions afforded RRE constructs the ability to bind with rev, while acting as reporter groups for binding of rev and inhibitor ligands, such as Neomycin B. This fluorescence approach has revealed the rev binding is a two-step process involving structural isomerization of the RNA, and that inhibitor ligands generally bind to both tight and weaker sites on RRE, where one of the weaker sites is inhibitory to rev binding.

Figure 3:
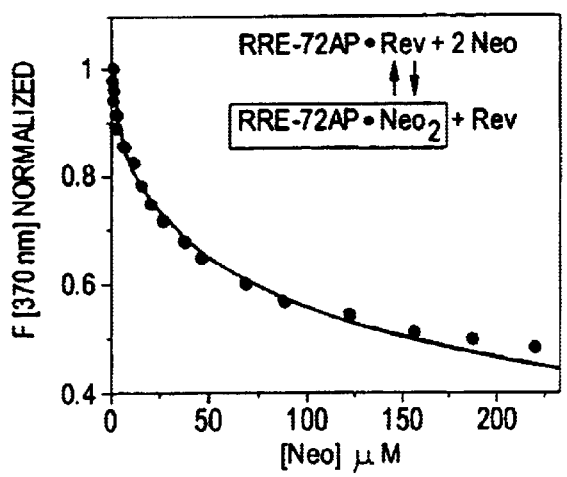
FIG. 3 is a graph showing the change in level of fluorescence when a RRE-72AP+rev complex is titrated with Neomycin B.

Quantitative analysis of the binding event indicates the rev peptide binds to 2-AP RRE with wild type affinity ($K_D$~13±2 nM). The fluorescent 72AP-RRE construct is also a useful probe for assaying small molecule binding to RRE, as well as determining if the small molecule is an effective inhibitor of the rev-RRE interaction. For example, it has been shown using the aminoglycoside Neomycin B, a known inhibitor of RRE-rev interaction, that the 72AP-RRE construct can be used to detect small molecule inhibition of the rev-RRE interaction. Addition of Neomycin B to the 72AP-RRE-peptide complex (1:1) results in a restoration of the original level of fluorescence observed for the 72AP-RRE, shown in FIG. 3. Specifically, FIG. 3 demonstrates that when the concentration of Neomycin B is nearly 0 M, a normalized fluorescence of 1 is observed. As Neomycin B is introduced, rev is removed from the 72-AP-RRE complex in favor of Neomycin. Using the Dynafit program, it was calculated the Neomycin B binds to a first tight site ($K_D$~0.23 $\mu$M) and then competitively with rev for a second site ($K_D$~1.9±0.6 $\mu$M).

As described in *Biochemistry*, Vol. 39, No. 19, p. 5630–5641, herein incorporated by reference in its entirety, stopped-flow kinetic experiments indicate rev binding to 72AP occurs in two distinct phases, suggesting a two-phase binding system. The faster binding event is found to be linearly dependent upon rev concentration, while the second, slower phase follows a hyperbolic dependence on rev concentration.

Figure 4:
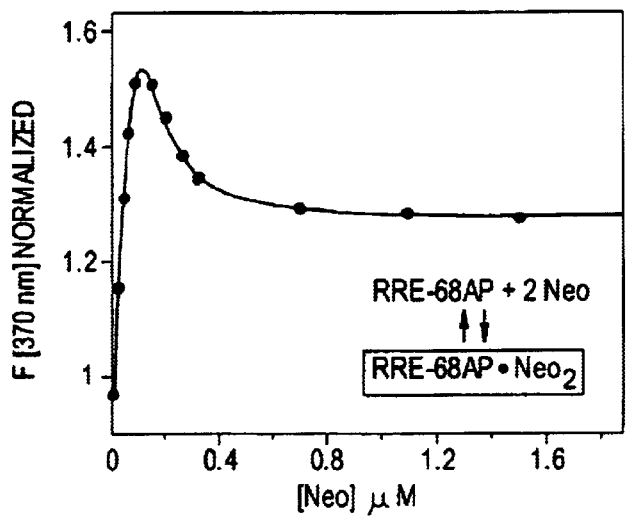
FIG. 4 is a graph showing the change in the level of fluorescence with RRE-68 is titrated with Neomycin B.

From experiments, the location of rev binding to RRE has been determined. When rev is titrated with 68AP-RRE, no significant change in fluorescence results (FIG. 4). While this may indicate that incorporation of 2-AP at position 68 prevents binding of rev to RRE, a competition binding experiment described in *Biochem*. Vol. 39, No. 19, 5630, indicates otherwise. Therefore, it can be concluded that because 72AP-RRE+rev causes a conformational change near position 72, as observed through an increase in fluorescence, and 68AP-RRE+rev causes no conformational change near position 68, as observed through no change in fluorescence, it is can be concluded that rev binds with RRE in the vicinity of position 72.

As described, the 68AP-RRE construct does not indicate rev peptide binding, but is used to directly detect binding of small molecules with RRE. For example, using the 68AP-RRE construct, three classes of binding sites for the Neomycin B can be detected. The first site is non-inhibitory to rev binding ($K_D$=0.24±0.040 $\mu$M), the second site inhibited rev binding in a competitive fashion ($K_D$=1.8±0.08 $\mu$M), and the third class of sites is attributed to non-specific binding ($K_D$~40 $\mu$M). In addition, the low affinity binding interaction ($K_D$=1.5 $\mu$M) of a second aminoglycoside, Streptomycin, with RRE could also be detected and compared to the Neomycin binding data. The Streptomycin binding data was collected to show that the observed fluorescence perturbations were not specific to Neomycin B, but rather a general probe for any ligand that may interact with RRE.

Figure 5:
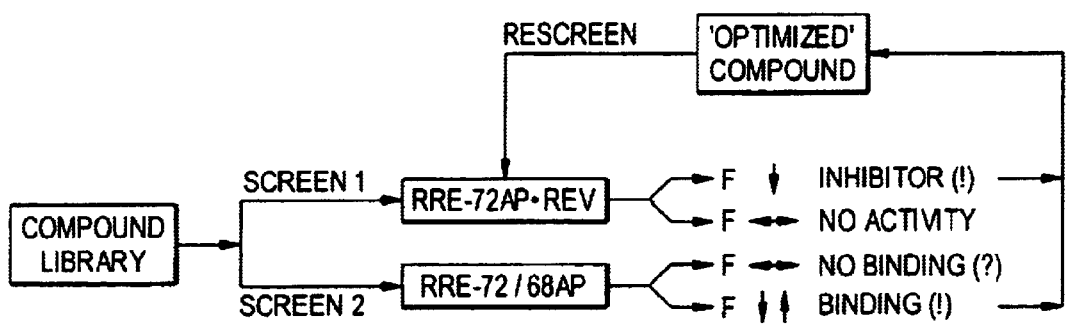
FIG. 5 is a schematic representation of a dual 2-AP screening process.

Following a first screening, using both screens 1 and 2, as indicated in FIG. 5, if the ligand binds or otherwise shows an indication of a possibility of being an effective inhibitor, chemical changes can be effected, either rational or combinatorial, to develop new ligands from the lead compound which are hopefully optimized for inhibition. Repetitive optimization, including incremental changes, can continually make slight changes to discover the most effective form of the ligand. This optimization step is also used to measure the inhibition constant ($K_I$) to determine the efficacy of inhibition, as compared to the lead ligand and other ligands.

Synthesis of the 2-AP labeled RRE RNA oligonucleotides and the experimental setup for the detection of the fluorescence emission perturbation given below is provided as a non-limiting example.

Figure 1:
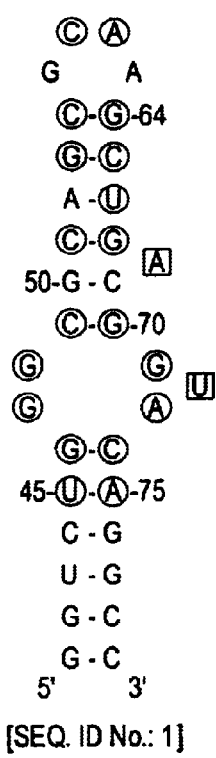
FIG. 1 represents a sequence of the truncated 34mer RNA hairpin derived from the RRE stem-loop IIB hairpin with added 2-AP at positions A68 and U72.
Figure 2:
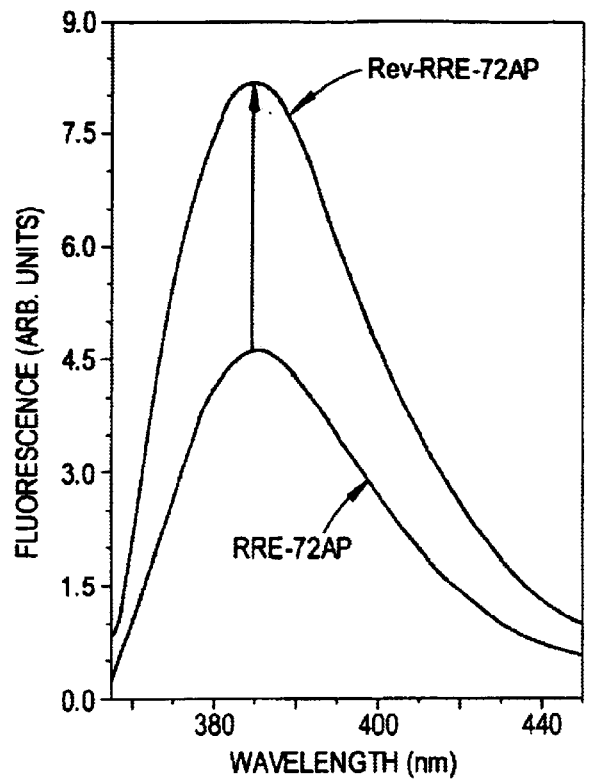
FIG. 2 is a graph showing fluorescence of modified RRE alone and in the presence of modified RRE.

The 34mer RNA hairpin, shown in FIG. 1, containing the high affinity rev binding site was prepared in vitro T7 polymerase run-off transcription using a synthetic DNA oligonucleotide template using the method of Milligan and Uhlenback. DNA templates were purchased from Integrated DNA Technologies (Coralville, Iowa), and purified using preparative-scale denaturing polyacrylamide gel electophoresis. 2-aminopurine 2=-O-methyl riboside containing RNA oligonucleotides were synthesized on an Applied Biosystems 390 synthesizer (Perkin-Elmer, Forest City, Calif.) using standard phosphoramidite chemistry. The nucleoside phophoramidites were purchased from Glen Research (Sterling Va.). All RNA oligonucleotides were purified using preparative-scale denaturing polyacrylamide gel electrophoresis and recovered by electrophoretic elution. RNA samples were desalted by extensive dialysis against DEPC treated dd$H_2O$ using a microdialysis system. RNA concentrations were determined by measuring the absorbence at 260 nm using an extinction coefficient of 322.9 n$M^{-1}cm^{-1}$. The arginine-rich peptide(Suc-TRQARRNRRWRERQRAAAK SEQ ID NO: 9) used in this process was derived from the rev protein and is known to interact with high affinity to RRE stem-loop IIB. The peptide was synthesized by Rio Synthesis, Inc (Lewisville, Tex.) and purified using C-18 reverse-phase HLPC to a final purity of greater than 95%. MALDI-TOF (Perseptive Biosystems, Framington, Mass.) analysis gave a MW [MH+]=2950.2, which is in line with the theoretical mass of 2950.3. The rv concentration was determined from its extinction coefficient at 280 nm (5.6 m$M^{-1}cm^{-1}$). Neomycin B and streptomycin aminoglycosides were purchased from Sigma (St. Louis, Mo.) and used without further purification. All other buffers end reagents were of the highest commercially available quality and were used without further purification.

The fluorescence of RNA oligonucleotide samples (150 $\mu$L), selectively labeled with 2-AP, was measured at 10° C. on a SPEX Fluoromax-2 spectrofluorometer (Instruments, SA, Edison, N.J.) using a 0.3 cm square cuvette. RRE sample concentration was typically 100 nM in either standard buffer A (140 mM NaCl, 5 mM KCl, 1 mM $MgCl_2$, 1 mM $CaCl_2$, and 20 mM HEPES [7.4 pH]) or buffer B (25 mM NaCl, 5 mM KCl and 1 mM Cacodylate [6.5 pH]). Emission spectra were recorded over the wavelength range of 330 to 450 nm with an excitation wavelength of 310 nm. The spectral bandpass was 5 nm for all spectra. The dissociation constant for rev binding to RRE-72AP was determined by following the increase in fluorescence at 370 nm as a fixed concentration of the fluorescent RNA was titrated with increasing amounts if rev. Similarly, the binding of aminoglycosides was followed by monitoring the change in 2-AP fluorescence as a fixed concentration of RRE-72AP or RRE-68AP was titrated with increasing amounts of the aminoglycoside. Single site binding of rev or aminoglycoside was fitted to Formula I:

$$F = -\{(F_o - F_f)/2 * [RRE]_{tot}\}\{b - \sqrt{(b^2 - 4[L]_{tot}[RRE]_{tot})}\} + F_o \quad (1)$$
$$b = K_d + [L]_{tot} + [RRE]_{tot}$$

where $F_o$ and $F_f$ are the initial and final fluorescence intensities, respectively, $[RRE]_{tot}$ is the total RRE concentration, and $[L]_{tot}$ is the total concentration of rev, aminoglycoside or other ligands. Aminoglycoside binding to multiple sites on RRE was modeled using the computer program Dynafit. Competitive displacement assays were performed to determine which aminoglycoside binding were inhibitory to rev binding. For these experiments, a solution of 2-AP labeled RRE was incubated with a fixed concentration of Neomycin B (or rev peptide), and the fluorescence change followed as increasing amounts of competing rev peptide (or Neomycin B) was added to the solution. The fluorescence emission intensities at 370 nm as a function of total added ligand concentration were fit to a given molecular mechanism by non-linear least squared regression using the computer program Dynafit.

The 2-AP fluorescence binding assay described above can be adapted as the core technology in a dual detected high-throughput screen, based on a 96/384 well format fluorescence plate reader, where compounds in small molecule/combinatorial libraries could be assayed in parallel for direct binding affinity to RRE and inhibitory effects on RRE-rev interactions. FIG. 5 shows just such a process, where F plus a directional arrow is provided to indicate a change in fluorescence. Screen 1 is used to monitor inhibition, while screen 2 is used to monitor small molecule binding. Using this approach, both high affinity binders, as well as inhibitory binders would be identified simultaneously. This dual screen rapidly provides a wealth of information on what class of compounds binds tightly to RRE and which of these classes of molecules actually inhibit rev-RRE interactions. Such preliminary screening data could be very powerful when employed in design optimization of lead pharmaceutical compounds.

Therefore, the assay method of the present invention via a dual screen identifies the efficacy of a candidate compound or ligand in inhibiting the binding of rev to RRE in the following manner. First, the ligand is titrated to a solution containing a known concentration of rev and 72AP-RRE+rev and the change in fluorescence measured at 370 nm is noted. When the change in fluorescence is compared to FIG. 5, it can be seen that a decrease in fluorescence as the concentration of the ligand increases indicates that this particular ligand is likely an inhibitor for the formation of the rev-RRE complex. Using FIG. 3 and Formula I, the dissociation constant ($K_D$) for the particular ligand can be calculated with respect to 72AP-RRE.

Running the same procedure with 68AP-RRE will yield small molecule binding data, with no indication of inhibition. Therefore, it is preferred to run the procedure a second time using 2-AP in positions 72 and 68. If the result of screen 1 (using the ligand with 72AP-RRE+rev) produces no change in fluorescence, there is no need analyze screen 2, because the particular ligand does not cause a conformational change near position 72, and therefore, does not likely compete for binding with rev.

Screen 2, on the other hand, indicates interaction with RRE at either position 72 or 68 or both. The high throughput screen (HTS) of the present invention includes running screens 1 and 2, as shown in FIG. 5, simultaneously, to increase the amount of data obtained in a given period of time. Screen 1, using 72AP-REE+rev is designed to detent for ligands which inhibit interaction of RRE and rev, and screen 2, using 68/72AP-RRE SEQ ID NO: 2, is designed to detect ligands that simply bind to the RNA target.

Although screen 1 can be used alone to detect inhibitory ligands, screen 2 is used for other reasons. First, if both screens report binding, screen 2 can be used to determine if the particular ligand actually targets the RNA component of the complex or the protein. Additionally, screen 2 can reveal if the ligand binds to the RNA target, but does not inhibit the protein interaction (when taken in combination with the results of screen 1). Ligands, which bind but do not inhibit may, nevertheless, be useful after the above-described optimization step as leads for further modification, or may be useful in rational drug design because one could design against binding according to the modes of small molecules.

The methods described above are also transposable to the design of other fluorescent binding assays, using either 2-AP or other fluorescent nucleotide base analogs, to detect other nucleic acid interactions and the inhibition of complexes involving nucleic acid by small molecule antagonists. Examples include the FREP method to detect quantitative binding to nucleic acid targets, such as the dimerization initiation site (DIS) of HIV-1, as a second embodiment of the present invention. Maturation and packaging of HIV-1 virus requires self-association of the RNA retroviral genome, which is mediated in part by the DIS stem-loop within the Psi element of the genomic RNA retroviral protein NCp7. It is known that a homodimeric loop-loop "kissing" interaction is mediated by complementary nucleotides of the DIS hairpin structure. The loops of the putative DIS hairpin can form a homodimeric "kissing" complex with six base pairs. The remaining DIS loop purine nucleotides can potentially form non-canonical purine-purine or triplet type interactions. Disruption of this DIS homodimeric RNA-RNA stem-loop complex, which is a critical linkage point between the two packaged copies of the HIV-1 RNA genome found in all viral particles, may provide a potent drug against AIDS.

The FREP method described above including the incorporation of 2-AP can be used to quantify formation of RNA-RNA dimers or inhibition thereof. As in the rev-RRE model system, DIS can be used to demonstrate the utility of the FREP approach for rapid detection of this critical RNA-RNA interaction and potential drug antagonist binding to this nucleic acid target. Several RNA nucleotides were synthesized (using the same protocol as described for the RRE model system using standard RNA solid-phase synthesis) to contain the 2-AP-2'-O-methyl analog in naturally occurring adenosine base positions in the loop of the hairpin. Due to the dimeric interactions described above, the homodimeric RNA complex was converted to a heterodimeric system by strategic point mutations [U10→A/C and A13→G/U] in the naturally occurring loop sequence used in accordance with the invention.

FIG. 6 shows the different DIS sequences. FIG. 6a shows a wild-type DIS RNA oligonucleotide that spontaneously forms a homodimer in the presence of appropriate buffer conditions. FIGS. 6b and 6c indicate the structures of DIS-AG[4AP] and DIS-AG[12AP], wherein a substitution has been placed at positions 4 and 12, respectively. A DIS-UC construct is shown in FIG. 6d, forming an analogous heterodimer with the adenosine positions substituted with 2-AP boxed.

Using the DIS-AG[12AP] construct, the dimerization binding constant for the heterodimeric DIS-AG/DIS-UC hairpin was measured and quantified. As discussed above with reference to the rev-RRE system, the 2-AP fluorescent method proved to be a highly sensitive and efficient method for quantifying this RNA-RNA binding interaction, having a 5 to 10 fold increase in the fluorescence quench. In addition, competition experiments based on the use of this large fluorescence quench is entirely suitable for high-throughput screening of inhibitors of the HIV-1 DIS dimmer formation. The binding kinetics for formation of the immediate RNA complex has also been measured, as well as the structural rearrangement of the RNA dimer from the intermediate loop-loop interaction to the mature bulge duplex dimer using the FREP method of the invention.

Figure 6A:
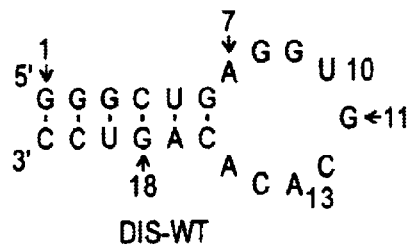
FIGS. 6A–6D represent wild type and modified HIV-1 dimerization initiation site sequences (DIS).
Figure 6B:
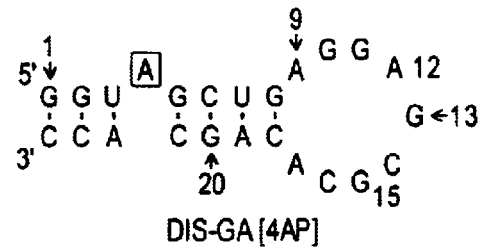
Figure 6C:
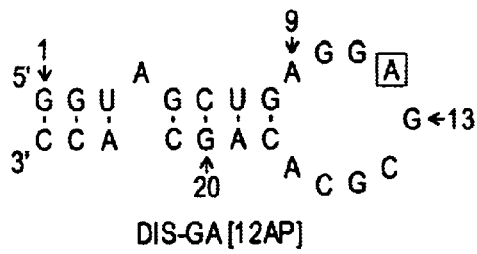
Figure 6D:
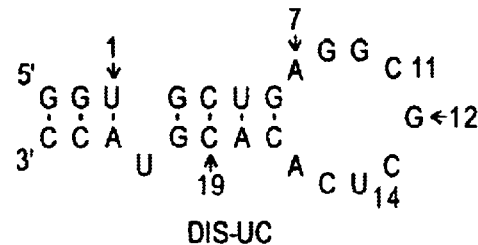

The model 2-AP heterodimeric DIS system has also been designed to monitor nucleoclapsid protein (NCp7) catalyzed maturation of the DIS structure. Maturation of the viral genome fold/packaging after encapsulation involves a critical RNA-RNA refolding event centered on the DIS hairpin in the dimerization localization sequence (DLS) and chaperoned by NCp7. Using specially designed DIS hairpins with the 2-AP incorporated into the bulge positions, as shown in FIGS. 6b and 6c, the stems, the kinetics of the DIS hairpin dimer refolding has been tracked, from the intermediate meta-stable loop-loop complex to the mature duplex form.

Because the NCp7 mediated refolding event appears to require the formation of the intermediate RNA complex, which is recognized by NCp7, the system can be inhibited in the presence of antisense RNA competitors designed to prevent the RNA-RNA complex formation. As with RRE-rev, this system can screen small molecules that may act to inhibit either the DIS mediated RNA dimerization or the specific chaperone activity of NCp7 mediated maturation of the DIS dimer.

In a third embodiment of the invention, FREP is used to monitor the binding of a type IB topoisomerase (topo) to its DNA target. These enzymes are key targets of anticancer drugs, and several of the most clinically effective chemotherapeutic agents target this enzyme. To monitor topo binding to DNA, the 2-AP label was placed next to the consensus binding sequence, shown below.

5'-CGTGTCGCCCTTCTTCCG-3'        [SEQ ID NO:10]

3'-CGACAGCGGGAATAAGGCTATCAC-5'  [SEQ ID NO:10]

This sequence is the preferred substrate for topo I from Vaccinia virus (18AP/24). The enzyme binds specifically to the consensus sequence CCTTT. Placement of the 2-AP label (N) adjacent to this sequence does not perturb the binding reaction, but provides a useful probe to monitor the topo interaction with the DNA.

Although described with reference to preferred embodiments, it should be readily understood that various changes and/or modifications could be made to the invention without departing from the spirit thereof. In any event, the invention is intended to be limited only by the scope of the following claims.

We claim:

1. A method, for monitoring and screening for active ligands of nucleic acid targets, the method comprising;
   providing the nucleic acid target having been modified by the inclusion of 2-aminopurine;
   introducing a ligand so as to cause interactions between the ligand and the nucleic acid target; and
   measuring the interactions, wherein said measuring comprises the detection of any modulation in the fluorescence properties of the 2-aminopurine resulting from changes in the conformation of the nucleic acid target bound by the ligand;
   wherein the target is a modified rev response element (RRE) having a stem-loop IIB, the stem-loop IIB comprising SEQ ID NO: 1.

2. The method of claim 1, wherein the modified rev response element (RRE) includes a 2-aminopurine at a position 72 of the stem-loop IIB.

3. The method of claim 2, wherein the rev response element (RRE) further includes a 2-aminopurine at position 68 of the stem-loop IIB.

4. The method of claim 1, wherein the rev response element (RRE) includes a 2-aminopurine at position 68 of the stem-loop IIB.

5. The method of claim 1, further comprising determining the fluorescence of the modified rev response element (RRE) prior to said introducing the ligand, and comparing the result of said determining to the result of said measuring to ascertain any difference in fluorescence.

6. The method of claim 1, wherein the ligand is an inhibitor of the binding of rev to the rev response element (RRE), and said measuring comprises determining a level of inhibition.

7. The method of claim 3, further comprising introducing rev to the RRE and ligand, wherein said measuring comprises determining a level of RRE-rev inhibition caused by the ligand.

8. The method of claim 7, further comprising: providing a modified RRE having a 2-aminopurine at positions 68 and 72 of stem-loop IIB; introducing the ligand to the modified RRE; and measuring interactions between the modified RRE and the ligand to determine a level of binding.

9. The method of claim 8, further comprising: optimizing the ligand following said measuring steps; providing the RRE including a 2-aminopurine at position 72 of a stem-loop IIB; introducing said optimized ligand to the RRE including a 2-aminopurine at position 72 of stem-loop IIB and rev; and measuring the level of inhibition caused by the optimized ligand.

10. The method of claim 9, further comprising: providing the modified RRE having a 2-aminopurine at positions 68 and 72 of stem-loop IIB;
    introducing the optimized ligand to a second unlabeled REE with altered sequence; and measuring interactions between the second REE and the ligand to determine a level of binding specificity between the modified REE and the optimized ligand.

11. A method for monitoring and screening for active ligands to a nucleic acid sequence comprising:
    providing a nucleic acid sequence, modified by the inclusion of 2-aminopurine; introducing a ligand; and
    measuring interactions between the nucleic acid sequence and the ligand as detected using 2-aminopurine fluorescence resulting from changes in the conformation of the nucleic acid target when bound by the ligand, wherein said sequence is a dimerization initiation site stem-loop.

12. The method of claim 11, wherein the dimerization initiation site stem-loop includes 2-aminopurine in at least one of the positions selected from the group consisting of a position 4 and position 12 of the sequence.

13. A method for monitoring and screening for active ligands to a nucleic acid sequence comprising: providing a nucleic acid sequence, modified by the inclusion of 2-aminopurine introducing a ligand; and measuring interactions between the nucleic acid sequence and the ligand as detected using 2-aminopurine fluorescence which may result from changes in the conformation of the nucleic acid target when bound by the ligand, wherein the sequence is a consensus binding sequence for a topoisomerase.

14. The method of claim 13, wherein the binding sequence includes SEQ ID NO: 10.

15. The method of claim 14, further comprising determining inhibition of interaction between DNA and the topoisomerase.

16. An assay kit for identifying a compound that inhibits the binding of HIV rev to HIV RRE comprising:

a ligand; to the RRE rev protein;

a modified RRE, having a stem-loop IIB comprising SEQ ID NO: 1, including 2-aminopurine; and means for determining any competitive inhibition of binding of rev to the modified REE by the compound.

17. The assay kit of claim 16, wherein the RRE includes 2-aminopurine at positions selected from only position 68, only position 72 and both position 68 and 72 of the stem-loop IIB.

18. The assay kit of claim 17, wherein said modified RRE includes 2-aminopurine at a position 72 of the stem-loop IIB.

19. The assay kit of claim 17, wherein said modified RRE includes 2-aminopurine at a position 68 and a position 72 of the stem-loop IIB.

20. The assay kit of claim 17, further comprising:

means for contacting the ligand with a modified REE, including 2-aminopurine at positions 68 and 72 of a stem-loop IIB; and a second means for determining a degree of binding between the ligand and the modified RRE, having 2-aminopurine at a position 68 and a position 72 of the stem-loop IIB.

21. The assay kit of claim 20, further comprising: an optimized ligand; modified RRE, having 2-aminopurine at position 72 of the stem-loop IIB; modified RRE, having 2-aminopurine at a position 68 and a position 72 of the stem-loop IIB means for determining change in binding of rev to modified RRE, having 2-aminopurine at position 72 of the stem-loop IIB, caused by said optimized ligand and means for determining the degree of binding between said optimized ligand and the modified RRE, having 2-aminopurine at positions 68 and 72 of the stem-loop IIB.

22. An assay kit for identifying a compound that inhibits the binding HIV rev to HIV RRE, comprising: a first modified RRE, including 2-aminopurine at a position 72 of a stem-loop IIB, the stem-loop IIB comprising SEQ ID NO: 1; and a second modified RRE, including 2-aminopurine at a position 68 and a position 72 of the stem-loop IIB, the stem-loop IIB comprising SEQ ID NO: 1.

* * * * *

SEQUENCE LISTING

<160> NUMBER OF SEQ ID NOS: 11

<210> SEQ ID NO 1
<211> LENGTH: 34
<212> TYPE: RNA
<213> ORGANISM: HIV

<400> SEQUENCE: 1
ggucugggcg cagcgcaagc ugacgguaca ggcc                             34

<210> SEQ ID NO 2
<211> LENGTH: 34
<212> TYPE: RNA
<213> ORGANISM: HIV
<220> FEATURE:
<221> NAME/KEY: misc_feature
<222> LOCATION: (23)..(23)
<223> OTHER INFORMATION: n is 2-aminopurine-2'0-methyl riboside
<221> NAME/KEY: misc_feature
<222> LOCATION: (27)..(27)
<223> OTHER INFORMATION: n is 2-aminopurine-2'0-methyl riboside

<400> SEQUENCE: 2
ggucugggcg cagcgcaagc ugncggnaca ggcc                             34

<210> SEQ ID NO 3
<211> LENGTH: 34
<212> TYPE: RNA
<213> ORGANISM: HIV
<220> FEATURE:
<221> NAME/KEY: misc_feature
<222> LOCATION: (23)..(23)
<223> OTHER INFORMATION: n is 2-aminopurine-2'0-methyl riboside

<400> SEQUENCE: 3
ggucugggcg cagcgcaagc ugncgguaca ggcc                                34

<210> SEQ ID NO 4
<211> LENGTH: 34
<212> TYPE: RNA
<213> ORGANISM: HIV
<220> FEATURE:
<221> NAME/KEY: misc_feature
<222> LOCATION: (27)..(27)
<223> OTHER INFORMATION: n is 2-aminopurine-2'0-methyl riboside

<400> SEQUENCE: 4
ggucugggcg cagcgcaagc ugacggnaca ggcc                                34

<210> SEQ ID NO 5
<211> LENGTH: 21
<212> TYPE: RNA
<213> ORGANISM: HIV

<400> SEQUENCE: 5
gggcugaggu gcacacaguc c                                              21

<210> SEQ ID NO 6
<211> LENGTH: 24
<212> TYPE: RNA
<213> ORGANISM: HIV
<220> FEATURE:
<221> NAME/KEY: misc_feature
<222> LOCATION: (4)..(4)
<223> OTHER INFORMATION: n is 2-aminopurine-2'0-methyl riboside

<400> SEQUENCE: 6
ggungcugag gagcgcacag caac                                           24

<210> SEQ ID NO 7
<211> LENGTH: 24
<212> TYPE: RNA
<213> ORGANISM: HIV
<220> FEATURE:
<221> NAME/KEY: misc_feature
<222> LOCATION: (12)..(12)
<223> OTHER INFORMATION: n is 2-aminopurine-2'0-methyl riboside

<400> SEQUENCE: 7
gguagcugag gngcgcacag cacc                                           24

<210> SEQ ID NO 8
<211> LENGTH: 24
<212> TYPE: RNA
<213> ORGANISM: HIV

<400> SEQUENCE: 8
ggugcugagg cgcucacagc uacc                                           24

<210> SEQ ID NO 9
<211> LENGTH: 23
<212> TYPE: PRT
<213> ORGANISM: HIV
<220> FEATURE:
<221> NAME/KEY: MISC_FEATURE
<222> LOCATION: (1)..(1)
<223> OTHER INFORMATION: Xaa is Suc

<400> SEQUENCE: 9

-continued

```
Xaa Thr Arg Gln Ala Arg Arg Asn Arg Arg Arg Arg Trp Arg Glu Arg
1               5                   10                  15

Gln Arg Ala Ala Ala Ala Lys
            20

<210> SEQ ID NO 10
<211> LENGTH: 18
<212> TYPE: DNA
<213> ORGANISM: HIV
<220> FEATURE:
<221> NAME/KEY: misc_feature
<222> LOCATION: (13)..(13)
<223> OTHER INFORMATION: N is 2-AP

<400> SEQUENCE: 10
cgtgtcgccc ttnttccg                                             18

<210> SEQ ID NO 11
<211> LENGTH: 24
<212> TYPE: DNA
<213> ORGANISM: HIV

<400> SEQUENCE: 11
cactatcgga ataagggcga cacg                                      24
```